US006498040B1

(12) United States Patent
Yokoyama et al.

(10) Patent No.: US 6,498,040 B1
(45) Date of Patent: Dec. 24, 2002

(54) HPLC APPARATUS FOR FRACTIONING AND PREPARING SAMPLE FOR NMR SPECTROMETRY AND METHOD OF CHANGING MOBILE PHASE

(75) Inventors: Yumi Yokoyama, Ibaraki-ken (JP); Naoya Kishi, Tsukuba (JP); Masayuki Tanaka, Tsukuba (JP); Naoki Asakawa, Tsukuba (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/463,491

(22) PCT Filed: May 26, 1999

(86) PCT No.: PCT/JP99/02783

§ 371 (c)(1),
(2), (4) Date: Feb. 10, 2000

(87) PCT Pub. No.: WO99/61905

PCT Pub. Date: Dec. 2, 1999

(30) Foreign Application Priority Data

May 26, 1998 (JP) ............................................. 10-144452

(51) Int. Cl.[7] .................. G01N 30/02; G01N 30/06
(52) U.S. Cl. ................... 436/161; 73/61.55; 73/61.56; 73/61.59; 210/198.2; 210/656; 210/662; 324/307; 422/70; 436/173; 436/178
(58) Field of Search ................... 436/161, 173, 436/178; 422/70; 324/307; 73/61.52, 61.55, 61.56, 61.59; 210/656, 662, 198.2

(56) References Cited

FOREIGN PATENT DOCUMENTS

JP 6-256227 9/1994

OTHER PUBLICATIONS

Magnetic Resonance in Chemistry, 36 (1998), Mar. 13, 1998, pp. 104–109, L. Griffiths, "Optimization of LC–NMR III–Increased Signal–to–Noise Ratio Through Column Trapping".

Chromatographia, 47 (1998), Mar. 1998, pp. 264–270, E. Clayton, "The Application of High Performance Liquid Chromatography, Coupled to Nuclear Magnetic Resonance Spectroscopy and Mass Spectrometry . . . ".

Anal. Chem., 55 (1983), pp. 1611–1614, J. Buddrus, "Comparison of On–line and Off–line Liquid Chromatography/Nuclear Magnetic Resonance Spectrometry for Analysis of Steroid Mixtures".

JEOL Ltd., Nov. 7, 1980, Microfilm of the specification and drawings annexed to the request of Japanese Utility Model Application No. 54–52836 ( Laid Open #55–154470).

Chromatography, 19 (1998), Nov. 1998, pp. 262–263, Y. Yokoyama, "LC–NMR he no kisoteki na kentou".

Primary Examiner—Jan Ludlow
(74) Attorney, Agent, or Firm—Birch, Stewart, Kolasch & Birch, LLP

(57) ABSTRACT

A high-performance liquid chromatography apparatus and a process for conversion of mobile phase, enabling a trace amount of sample for NMR analysis to be efficiently separated and prepared, includes steps of separating a target ingredient from the sample by the high-performance liquid chromatography, trapping the target ingredient in a trapping column using a different mobile phase, replacing water by deuterium oxide and eluting this target ingredient from the trapping column using deuterated solvent other than deuterium oxide.

2 Claims, 4 Drawing Sheets

[min]

[min]

[ppm]

HPLC APPARATUS FOR FRACTIONING AND PREPARING SAMPLE FOR NMR SPECTROMETRY AND METHOD OF CHANGING MOBILE PHASE

BACKGROUND OF THE INVENTION

1. Technical Field

This invention relates to process and apparatus for mobile phase conversion in a high-performance liquid chromatography to achieve efficient separation and preparation of a sample for nuclear magnetic resonance (NMR) analysis.

2. Description of the Prior Art

The high-performance liquid chromatography (referred to hereinafter as HPLC, in certain cases) has usually been utilized as the technique to analyze a trace amount of ingredient contained in a sample.

Recently, the system has been also proposed, which comprises this HPLC combined with the mass spectrometer so that separation and identification of an ingredient can be achieved at once.

For example, Japanese Patent Application Disclosure Gazette No 1991-175355 describes the process and apparatus for mobile phase conversion in mass spectrometry utilizing the high-performance liquid chromatography. According to this disclosure, a target ingredient contained in the sample is trapped by the high-performance liquid chromatography and this target ingredient is transferred to the mass spectrometer by using the mobile phase which is different from the mobile phase for separation of the sample and suitable for the mass spectrometry.

Structure analysis utilizing NMR requires at least several hundred micrograms of sample and an initial sample as much as several hundred milligrams is required to separate, for example, 0.1% of impurities contained in drug substance.

Conventionally, separation of a NMR sample from a given initial sample has been carried out several times on each divided amount of said initial sample. Such procedure has disadvantageously taken much time to concentrate the NMR sample and, if the NMR sample is unstable, decomposition thereof has sometimes occurred during the step of concentration.

In NMR analysis, deuterated solvent such as deuterium oxide or deuterated methanol having every hydrogen atom replaced by deuterium which is its isotope. In view of the fact that such solvent is considerably expensive, there is a serious demand that the sample for NMR analysis should be prepared as efficiently as possible.

While the system comprising the high-performance liquid chromatography combined with NMR is well known as has already been described. However, it has been impossible for this system of well known art to inject an adequate amount of sample into the system because this system uses HPLC for analysis. Therefore, it has been difficult to isolate a trace amount, e.g., 0.1% of impurities contained in drug substance and to analyze its structure. Furthermore, a probe exclusively used for this purpose must be separately purchased and correspondingly increases a cost to use this system of prior art. From the viewpoint of the cost, there is a demand for a more simple and more convenient system.

In view of the problem of the prior art as has been described, it is a principal object of this invention to provide a system enabling separation, desalting, concentration and deuterium replacement of a trace amount of ingredient contained in a mixture to be achieved in on-line fashion particularly using an extremely small amount of expensive deuterated solvent such as deuterium oxide or deuterated methanol.

SUMMARY OF THE INVENTION

The object set forth above is achieved, according to one aspect of this invention, by a Process for mobile phase conversion in high-performance liquid chromatography to carry out separation and preparation of a sample for NMR analysis comprising steps of: separating ingredients contained in the sample by the high-performance liquid chromatography; trapping said ingredients in a trapping column using a different mobile phase; replacing water by deuterium oxide; and eluting target ingredients from said trapping column using a deuterated solvent other than said deuterium oxide.

The object set forth above is achieved, according to another aspect of this invention, by a high-performance liquid chromatography apparatus for separation and preparation of a sample for NMR analysis comprising; a separation/sampling section serving for separation of ingredients contained in the sample using high-performance liquid chromatography; a trapping section serving to trap said ingredients in a trapping column using a different mobile phase; a deuterium oxide replacement section serving to replace water by deuterium oxide; and a deuterated solvent supplying section serving to supply a deuterated solvent other than said deuterium oxide and thereby to elute the target ingredients from said trapping column.

The novel process enables separation and preparation of a target compound suitable for NMR analysis to be simultaneously as well as efficiently achieved. This is owing to the steps of concentration and mobile phase conversion carried out during separation of a trace amount of ingredient contained in a sample by high-performance liquid chromatography.

According to one preferred embodiment of the high-performance liquid chromatography apparatus provided in the form of a system including pumps, injector, separation column, switching valves, distribution valve, sampling loop and trapping column, said system comprising: a separation/sampling section comprising a pump (P1) actuated to supply a mobile phase for separation of the sample, a detector to detect a peak of a desired compound, and valves (V1), (V2), (V3), wherein said desired compound flows through said valve (V1) into a loop (LOOP) extending between said valve (V2) and said valve (V3) so as to be accumulated in said loop (LOOP); a trapping section comprising a pump (P2) actuated to supply a mobile phase for concentration of the sample so as to flow through said valve (V1), said valve (V2), said loop (LOOP), said valve (V3), a valve (V4), a valve (V5), a trapping column (TC) and said valve (V4) in this order, and a distribution valve (R) serving to mix the flow with said mobile phase for concentration of the sample between said valve (V3) and said valve (V4) so that the desired compound may be concentrated in said trapping column (TC); a deuterium oxide replacement section comprising a pump (P3) actuated to supply deuterium oxide so as to flow said valve (V5), said trapping column (TC) and said valve (V4) in this order and to replace water by deuterium oxide; and a deuterated solvent supplying section comprising a pump (P4) actuated to supply deuterated solvent other than deuterium oxide so as to flow through said valve (V4), said trapping column (TC), said valve (V5), said valve (V4), said analytical column (AC) and a detector (D2) so that the desired compound may be obtained for NMR analysis.

The term "pump" used herein should be understood to be the liquid pump exclusively used for high-performance liquid chromatography. The term "valve" used herein should be understood to be the 6-way valve or the like usually used for high-performance liquid chromatography.

The term "analytical column" used herein should be understood to include various separation columns usually used for high-performance liquid chromatography. Such preparative column is not limited to so-called normal column, reverse column, GPC column or the like. The column may be selected from the various columns so far it is effective to separate a trace amount of target ingredient contained in a sample.

The term "trapping column" used herein should be understood to be. the column adapted to trap and concentrate the target ingredient. This is not limited to the column exclusively used for high-performance liquid chromatography but any other column may be used so far as it has a desired pressure resistance .

The term "sampling loop" used herein should be understood to be a capillary tube adapted to accumulate ingredient separated from the sample by the separation column and, in most cases, stainless tube is used for this purpose. Length of this tube may be adjusted depending on factors such as a concentration of the ingredient.

The pumps, the columns, the valves and the like are usually connected one to another by the stainless tubes.

The term "deuterated solvent" used herein should be understood to be the solvent (other than deuterium oxide) having its every hydrogen atom replaced by deuterium such as deuterated methanol, deuterated acetonitrile, deuterated chloroform or deuterated methylene chloride. Of these, the deuterated methanol is often used as this deuterated solvent.

Conversion of the mobile phase used for high-performance liquid chromatography is carried out several times in accordance with this invention. The specific procedure of such mobile phase conversion will be more fully understood from the following description of the preferred embodiment. However, it should be understood that this invention is not limited to such preferred embodiment but various modifications are possible without departing from the scope of this invention.

DETAILED DESCRIPTION OF THE PREFERRED EMBODIMENTS

The invention will be described in details with reference to the accompanying drawings.

Figure 1:
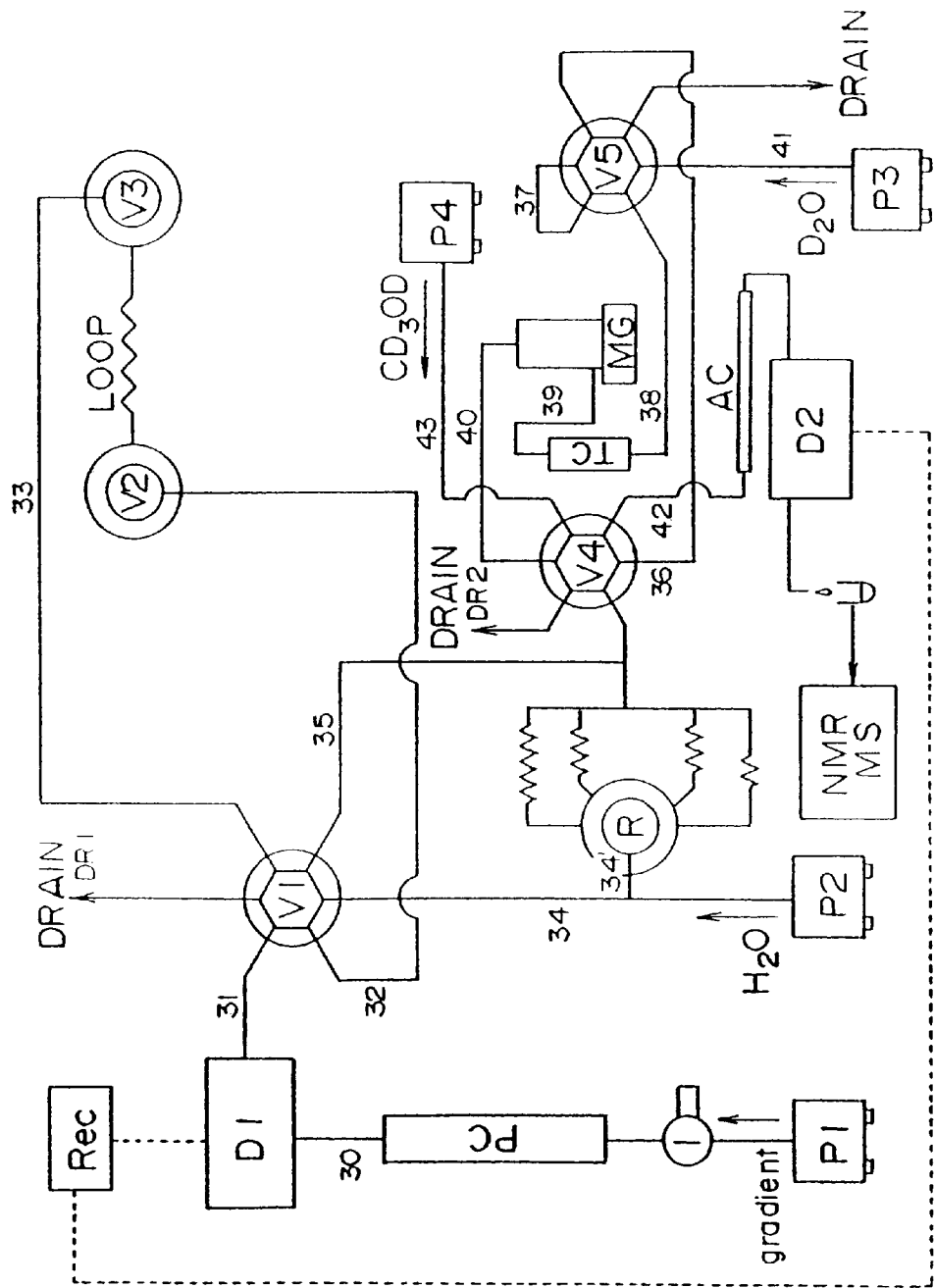
FIG. 1 is a block diagram illustrating the apparatus of the invention by way of example.

FIG. 1 illustrates ail apparatus for sample concentration and solvent conversion utilizing a high-performance liquid chromatography.

A section starting from a pump (P1) is a separation/sampling section.

The separation/sampling section comprises said pump (P1) in fluid-communication with a container filled with a mobile phase used to separate a target ingredient, an injector (I), a preparative column (PC), a detector (D1), a recorder (Rec). In addition to these parts, this section comprises a 6-way valve (V1) and valves (V2, V3) serving for line switching and a sampling loop (LOOP).

A drain (DR1) connected to said 6-way valve (V1) serves to discharge useless ingredients together with the mobile phase. All of drains (DRAIN) inclusive of said drain (DR1) are connected to the respective valves via lines usually made of stainless tubes.

Upon switching of the 6-way valve (V1), a line (32) is connected to said sampling loop (LOOP) which is, in turn, connected to switching valves (V2, V3)and the mobile phase is discharged from the drain (DR1).

A plurality of sub-loops are connected to the sampling loop (LOOP) and a passage for the mobile phase can be selectively connected to a desired one of said sub-loops by operating the switching valves (V2, V3).

In this manner, the ingredient having been separated in the separation/sampling section can be accumulated in the sub-loop assigned to this ingredient. The number of these sub-loops may be appropriately selected.

A section starting from a pump (P2) is a trapping section.

The trapping section comprises said pump (P2) adapted to supply a mobile phase of a composition different from the composition of said mobile phase serving for separation, the 6-way valve (V1), the valves (V2, V3) and the sampling loop (LOOP) which are common to said separation/sampling section. The trapping section further comprises 6-way valves (V4, V5), a trapping column (TC), a mixing chamber (MG), and a distribution valve (R) provided in a sub-passage branched from said passage. The mobile phase is discharged from a drain (DR2) connected to said valve (V4).

The trapping column (TC) functions to adsorb the target ingredient and may be a column presenting the same mode of separation as presented by the preparative column (PC). It should be understood that a column other than those exclusively used for the high-performance liquid chromatography may be used for this purpose so far as it is the column has a desired pressure-resistance.

Both the column (PC) and the column (TC) may be selected from a group including columns having various modes of separation such as normal column, reverse column, ion exchange column, affinity chromatography column and GPC column depending on a particular substance to be separated and analyzed.

A section starting from a pump (P3) is a deuterium oxide replacement section.

The deuterium oxide replacement section comprises said pump (P3) serving to supply deuterium oxide and the parts common to said trapping section, i.e., the 6-way valve (V5), the trapping column (TC), the mixing chamber (MG) and the 6-way valve (V4). The respective parts are connected one to another usually by means of stainless tubes and the deuterium oxide is discharged from the drain (DR2).

A section starting from a pump (P4) is a deuterated solvent supplying section.

The deuterated solvent supplying section comprises, in addition to said pump (P4) serving to supply deuterated solvent such as deuterated methanol (except deuteriun oxide), the 6-way valve (V4), the mixing chamber (MG), the trapping column (TC), the 6-way valve (V5) common to the deuterium oxide replacement section. The deuterated solvent supplying section further comprises a analytical column (AC) and a detector (D2) both being not common to said deuterium oxide replacement section.

The mixing chamber functionally corresponds to the solvent mixing column as disclosed in Japanese Patent Application Disclosure Gazette No. 1993-180820. Specifically, the chamber is previously filled with solvent different from the mobile phase and enables a gradient analysis to be easily performed. In accordance with this invention, the mixing chamber is useful to improve a quality of the purified and concentrated target ingredient by conducting the separation analysis also before separation/preparation of the sample for NMR. However, the mixing chamber is not the feature which is essential to this invention.

Now a process for solvent conversion utilizing the apparatus constructed as has been described above will be described in details.

The process starts with actuating the pump (P1) to supply the lines (30), (31) with the mobile phase for separation of ingredient and, at the same time, a sample containing the target ingredient is injected from the injector (I).

The sample containing various ingredients flows together with the mobile phase into the preparative column (PC) and is separated into these ingredients as the sample flows through said column (PC). The respective ingredients are monitored by the detector (D1) and the recorder (Rec).

All the ingredients other than the target ingredient are discharged from the drain (DR1).

The separated target ingredient is directed by switching the 6-way valve (V1) into the line (32) and then supplied to the sampling loop (LOOP) having its opposite ends connected to the switching valves (V2), (V3), respectively. The target ingredient is accumulated in the associated sub-loop by appropriately operating these switching valves (V2), (V3).

Switching of said valves (V2), (V3) are performed in response to detection signals output from the detector (D1) so that the target ingredient contained in the sample may be properly accumulated in the associated sub-loop.

It should be understood that the mobile phase for separation of the ingredients is discharged from the drain (DR1) via the line (33) and the valve (V1).

After an appropriate amount of the target ingredient has been accumulated in the sampling loop (LOOP) in this manner, the 6-way valve (V1) is switched to establish fluid communication between the lines (34) and (32).

Then, the pump (P2) is actuated to supply the sampling loop (LOOP) with the mobile phase (referred to hereinafter as the mobile phase for trapping) of a composition different from the composition of the ingredient separating mobile phase via the lines (34), (32) and the valve (V2). As a result, the target ingredient accumulated in the sampling loop (LOOP) is forced out together with the mobile phase for trapping from said sampling loop (LOOP). The target ingredient forced out in this manner flows through the line (33), the 6-way valve (V1), the 6-way valve (V4), the line (36), the 6-way valve (V5) and the lines (37), (38) into the trapping column (TC) and thereby the target ingredient is trapped in this trapping column (TC).

The mobile phase for trapping is discharged from the drain (DR2.) via the line (39), the mixing chamber (MG), the line (40) and the 6-way valve (V4).

At this step, a sub-passage (34') may be connected to the line (34) and thereby the mobile phase for trapping may be guided into the line (34) to facilitate the target ingredient to be trapped by the trapping column (TC).

The trapping column (TC) must be supplied with the mobile phase having the composition different from that of the mobile phase for separation in order to trap the target ingredient in said trapping column (TC). However, a serious problem would occur if the target ingredient accumulated in the sampling loop (LOOP) and the mobile phase for separation are forced out merely by the mobile phase for trapping. Specifically, these components should be mixed with the mobile phase coming from the sub-passage. Otherwise, a concentration of the mobile phase for separation would temporarily increase and trapping of the target ingredient would become difficult. A trapping efficiency is improved first when the mobile phase for separation is diluted by mixing this with the mobile phase for trapping coming from the sub-passage. A flow rate of this mobile phase for trapping may be regulated by the distribution valve (R) placed in the sub-passage.

The mobile phase for trapping causes the trapping column (TC) to trap the target ingredient. In addition, this phase functions to remove buffer contained in the mobile phase for separation accumulated in the sampling loop (LOOP). The mobile phase for trapping may be either of reverse phase type or of normal phase type. For example, water is useful for this purpose as the former type and hydrocarbons such as hexane or halogenated hydrocarbons such as chloroform are useful as the latter type.

Now the 6-way valve (V5) is switched to establish fluid communication between a line (41) and the line (38) and then the pump (P3) is actuated to supply the trapping column (TC) with deuterium oxide. Thus the mobile phase for trapping present in the trapping column (TC) and lines (38), (39), (40) is replaced by deuterium oxide.

It should be understood that, in this course, the ingredient present in the trapping column (TC) remain accumulated in this column and is not eluted.

Finally, the valves (V4), (V5) are switched to establish fluid communication from the pump (P4) to the detector (D2): via the lines (43), (40), the mixing chamber (MG), the line (39), the trapping column (TC), the line (38), the valve (V5), the line (37), (36), the valve (V4), the line (42), and the column for separation (AC). Thereupon, said pump (P4) is actuated.

The pump (P4) supplies deuterated solvent such as deuterated methanol (except deuterium oxide) by which the target ingredient accumulated in the trapping column (TC) is eluted. The target ingredient is further definitely separated/purified and further concentrated by the analytical column (AC). Thereafter the target ingredient flows through the detector (D2) and the desired separation/preparation is accomplished.

The invention will be more fully understood from the following description of an exemplarily conducted experiment.

In this experiment, Crotamiton containing approximately 2.5% of impurities was used as a sample and an effect of the apparatus and the process according to this invention was observed.

Specific experiment conditions pump 1(P1) . . . TOSOH CCPM mobile phase . . . $H_2O:CH_3CN=100:40$ separation column 1(PC) . . . ODS-AM,10×300 mm(YMC)

detector(D1) . . . detection wavelength UV 230 mm(Shimazu SPD-6A)

flow velocity . . . 4.0 ml/min
pump 2(P2) . . . TOSOH CCPM
mobile phase . . . H$_2$O(water)
flow velocity . . . 2.0 ml/min
trapping column(TC) . . . 4.6×34 mm(Inertsil)
trap time . . . 30 min
pump 3(P3) . . . TOSOH CCPM
mobile phase . . . D$_2$O(deuterium oxide)
flow velocity . . . 1.0 ml/min
conversion time . . . 10 min
pump 4(P4) . . . TOSOH CCPM
mobile phase . . . CD$_3$OD(deuterated methanol)
separation column(AC) . . . ODS, 2.1×250 mm(Inertsil)
detector(D2) . . . detection wavelength UV 230 mm(Shimazu SPD-6A)
flow velocity . . . 0.2 ml/min
NMR . . . JEOL JNM-α 400

Figure 2:
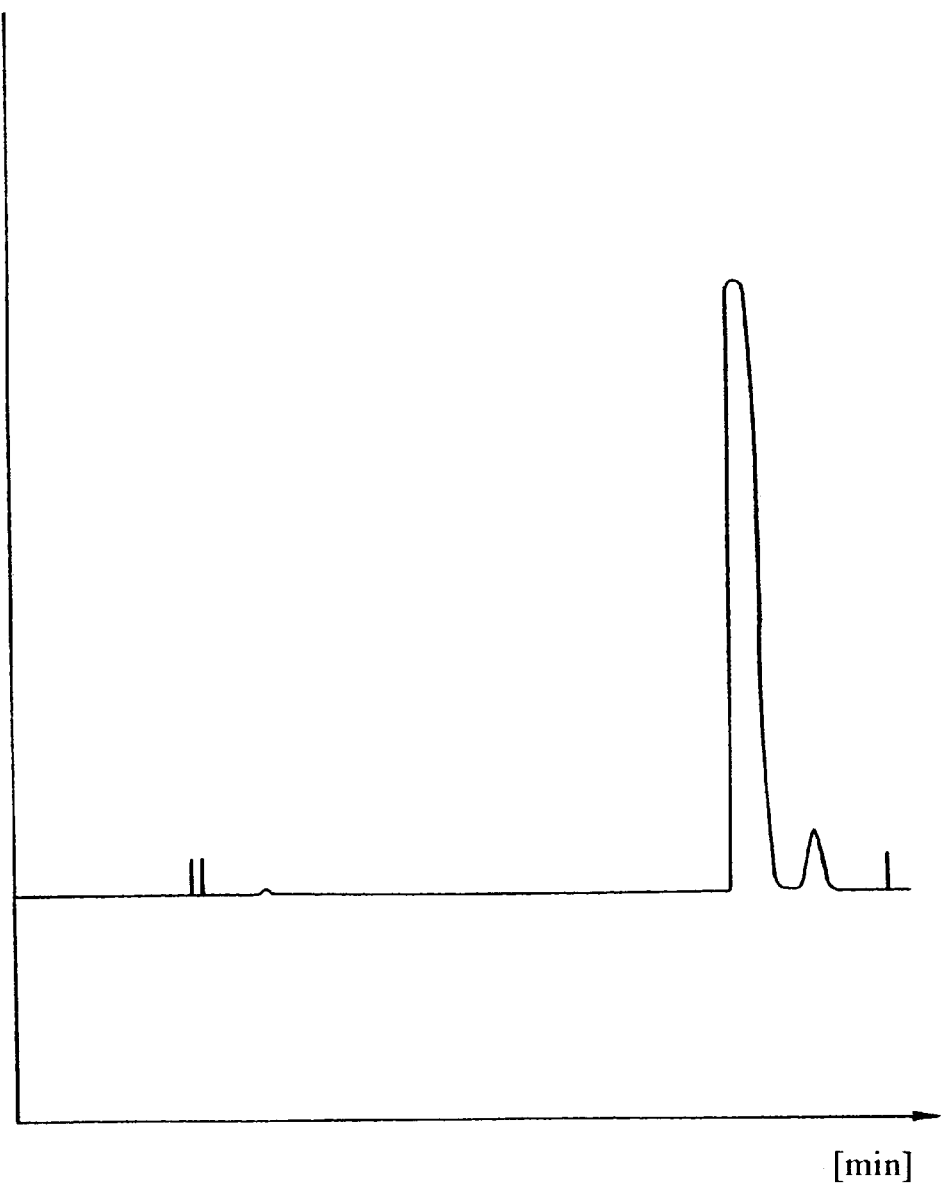
FIG. 2 is a chromatogram obtained by a detector D1 and a recorder in the apparatus of the invention.
Figure 3:
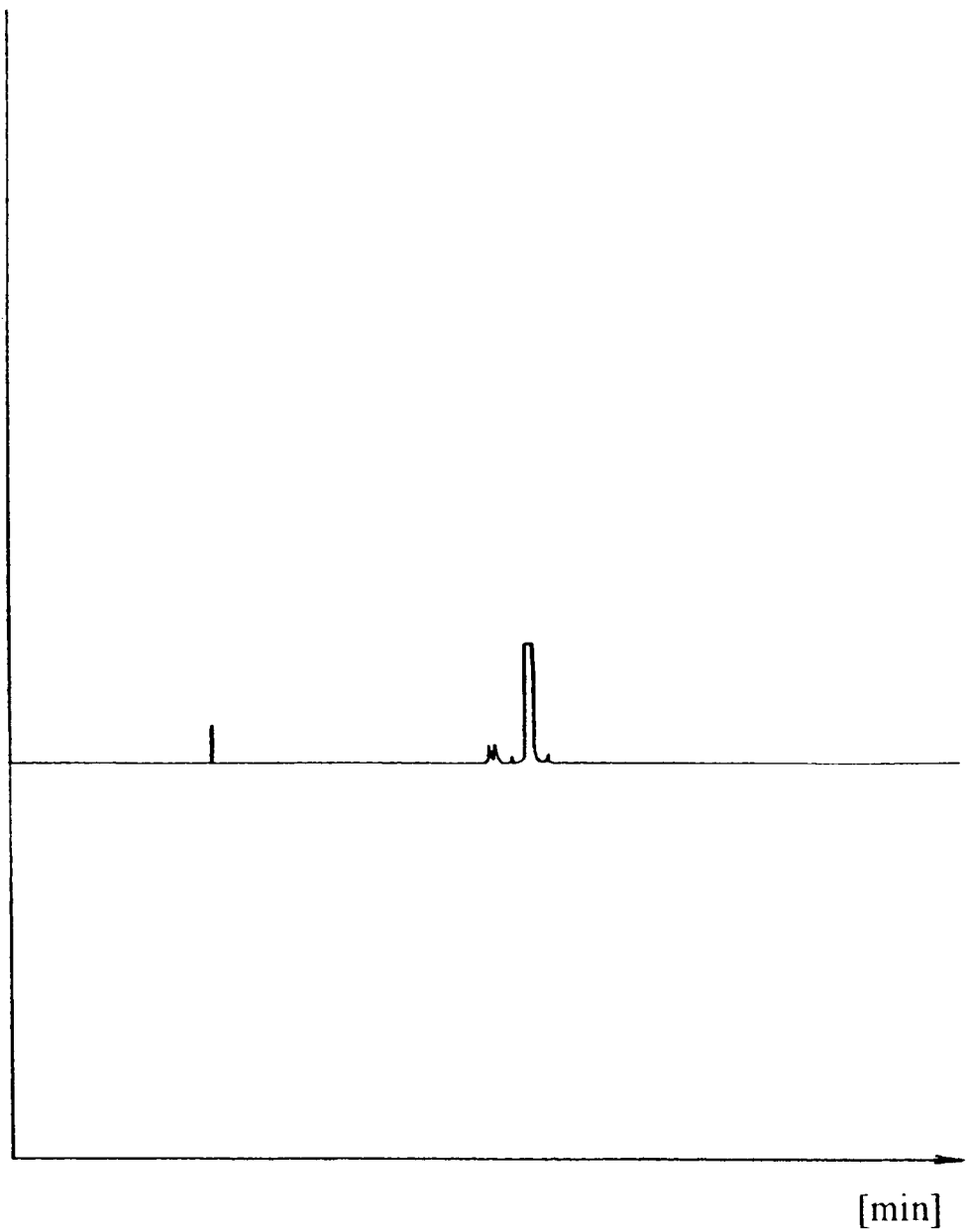
FIG. 3 is a chromatogram obtained by a detector D2 and a recorder in the apparatus of the invention.
Figure 4:
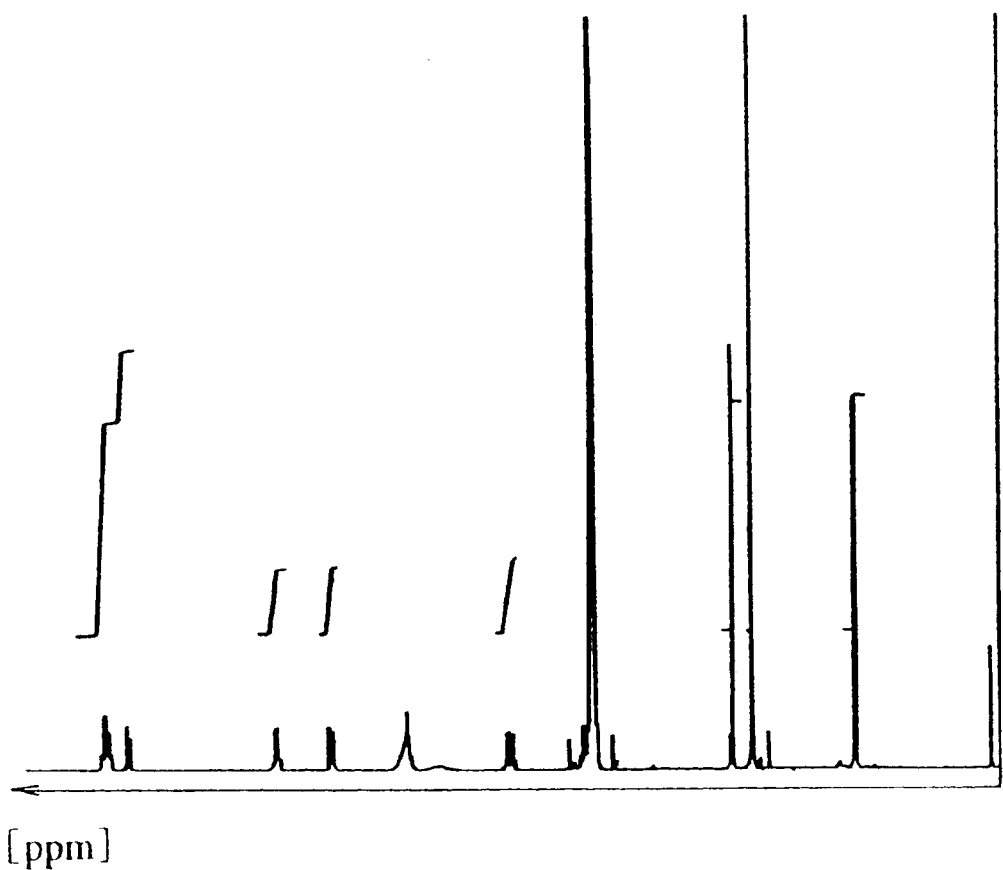
FIG. 4 is a NMR chart obtained using a sample for NMR analysis obtained by the apparatus of the invention.

As will be apparent from FIGS. 2 through 4 showing the result of this experiment, 10 ml of deuterium oxide and 4 ml of deuterated methanol were used.

Conventionally, NMR analysis has been conducted after separation, concentration and drying. In contrast with this, it has been found that the apparatus and the process provided by this invention enable the sample for NMR analysis to be obtained by on-line continuous processing. In addition, it has also been found that a desired effect is achieved by a trace amount of deuterated solvent such as deuterium oxide or deuterated methanol which is considerably extensive.

Industrial Applicability

This invention does not require a step of dry-up and particularly useful for structure analysis of unstable sample. This is for the reason that isolation and purification, desalting, concentration and deuterium replacement of respective ingredients contained in the sample to be structurally analyzed can be achieved by the on-line processing.

This invention enables also a trace amount of impurities contained in a physiologically active substance expected to be promising as a drug substance to be rapidly isolated and purified, desalted, concentrated and deuterium replaced.

Furthermore, this invention enables trace amounts of two or more ingredients contained in a sample to be separated one from another and facilitates replacement by deuterated solvent suitable for NMR analysis such as deuterated methanol. Additionally, this invention enables a used amount of such deuterated solvent to be substantially reduced.

What is claimed is:

1. A process for mobile phase conversion in high-performance liquid chromatography (HPLC) to carry out separation and preparation of a sample for NMR analysis, comprising the steps of:

separating a target ingredient from other ingredients contained in the sample by a high-performance liquid chromatography process with a separation column and a first mobile phase;

trapping said target ingredient in a trapping column using a second mobile phase that is different from said first mobile phase;

replacing said second mobile phase in said trapping column with deuterium oxide; and eluting said target ingredient from said trapping column using a deuterated solvent other than said deuterium oxide, said separating step further comprising a step of actuating a pump (P1) to supply said first mobile phase for separation of the sample in said separation column, a detector to detect a peak of said target ingredient, and valves (V1), (V2), (V3), wherein said target ingredient flows through said valve (V1) into a sampling loop (LOOP) extending between said valve (V2) and said valve (V3) so as to be accumulated in said sampling loop (LOOP);

said trapping step further comprising a step of actuating a pump (P2) to supply said second mobile phase for concentration of the sample so as to flow through said valve (V1), said valve (V2), said sampling loop (LOOP), said valve (V3), a valve (V4), a valve (V5), said trapping column (TC) and said valve (V4) in this order, and a distribution valve (R) serving to mix the target ingredient accumulated in said sampling loop with said second mobile phase for concentration of the sample between said valve (V3) and said valve (V4) so that the target ingredient may be concentrated in said trapping column (TC);

said replacing step further comprising a step of actuating a pump (P3) to supply deuterium oxide so as to flow through said valve (V5), said trapping column (TC) and said valve (V4) in this order and to replace said second mobile phase with deuterium oxide; and said eluting step further comprising a step of actuating a pump (P4) to supply deuterated solvent other than deuterium oxide so as to flow through said valve (V4), said trapping column (TC), said valve (V5), said valve (V4), said separation column (AC) and a detector (D2) so that the target ingredient may be obtained for NMR analysis.

2. A high-performance liquid chromatography (HPLC) apparatus for separation and preparation of a sample for NMR analysis, comprising:

a separation/sampling section having a separation column and a first mobile phase for separating a target ingredient from other ingredients contained in the sample by a high-performance liquid chromatography process;

a trapping section for trapping said target ingredient in a trapping column, using a second mobile phase that is different from said first mobile phase;

a deuterium oxide replacement section for replacing said second mobile phase in the trapping column with deuterium oxide; and a deuterated solvent supplying section for supplying a deuterated solvent other than said deuterium oxide to the trapping column, and thereby eluting the target ingredient from said trapping column, said separation sampling section further comprising a pump (P1) actuated to supply said first mobile phase for separation of the sample in said separation column, a detector to detect a peak of said target ingredient, and valves (V1), (V2), (V3), wherein said target ingredient flows through said valve (V1) into a sampling loop (LOOP) extending between said valve (V2) and said valve (V3) so as to be accumulated in said sampling loop (LOOP);

said trapping section further comprising a pump (P2) actuated to supply said second mobile phase for concentration of the sample so as to flow through said valve (V1), said valve (V2), said sampling loop (LOOP), said valve (V3), a valve (V4), a valve (V5), said trapping column (TC) and said valve (V4) in this order, and a distribution valve (R) serving to mix the target ingredient accumulated in said sampling loop with said second mobile phase for concentration of the sample between said valve (V3) and said valve (V4) so that the target ingredient may be concentrated in said trapping column (TC);

said deuterium oxide replacement section further comprising a pump (P3) actuated to supply deuterium oxide so as to flow through said valve (V5), said trapping column (TC) and said valve (V4) in this order and to replace said second mobile phase with deuterium oxide; and said deuterated solvent supplying section further comprising a pump (P4) actuated to supply deuterated solvent other than deuterium oxide so as to flow through said valve (V4), said trapping column (TC), said valve (V5), said valve (V4), said separation column (AC) and a detector (D2) so that the target ingredient may be obtained for NMR analysis.

* * * * *